United States Patent
Ohnota et al.

(10) Patent No.: US 6,770,133 B2
(45) Date of Patent: Aug. 3, 2004

(54) STABLE CRYSTAL OF THIAZOLIDINEDIONE DERIVATIVE AND PROCESS FOR PRODUCING THE SAME

(75) Inventors: Michiro Ohnota, Nagano (JP); Kazuo Orita, Saitama (JP)

(73) Assignee: Kyorin Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 10/257,939

(22) PCT Filed: Apr. 23, 2001

(86) PCT No.: PCT/JP01/03450
§ 371 (c)(1),
(2), (4) Date: Oct. 22, 2002

(87) PCT Pub. No.: WO01/81327
PCT Pub. Date: Nov. 1, 2001

(65) Prior Publication Data
US 2003/0101925 A1 Jun. 5, 2003

(30) Foreign Application Priority Data
Apr. 25, 2000 (JP) ........................ 2000-124006

(51) Int. Cl.[7] ................................. C30B 7/04
(52) U.S. Cl. .................... 117/68; 117/69; 117/925; 117/926; 117/927
(58) Field of Search .................... 117/68, 69, 925, 117/926, 927

(56) References Cited

U.S. PATENT DOCUMENTS

| | | | | |
|---|---|---|---|---|
| 4,687,777 A | * | 8/1987 | Meguro et al. | 514/342 |
| 4,725,610 A | * | 2/1988 | Meguro et al. | 514/369 |
| 4,864,028 A | * | 9/1989 | York, Jr. | 546/15 |
| 5,308,856 A | | 5/1994 | Ohnota et al. | |
| 5,342,850 A | | 8/1994 | Ohnota et al. | |
| 6,001,862 A | * | 12/1999 | Maeda et al. | 514/369 |
| 6,030,990 A | * | 2/2000 | Maeda et al. | 514/369 |
| 6,043,262 A | * | 3/2000 | Hayakawa et al. | 514/365 |
| 6,147,101 A | * | 11/2000 | Maeda et al. | 514/369 |

FOREIGN PATENT DOCUMENTS

| | | |
|---|---|---|
| JP | 8-217764 | 8/1996 |
| JP | 10-1476 | 1/1998 |
| WO | 96/38428 | 12/1996 |
| WO | 99/31095 | 6/1999 |

* cited by examiner

*Primary Examiner*—Robert Kunemund
(74) *Attorney, Agent, or Firm*—Oblon, Spivak, McClelland, Maier & Neustadt, P.C.

(57) ABSTRACT

A homogeneous crystal having excellent stability which is suitable for the industrial-scale production of 5-[(2,4-dioxothiazolidin-5-yl)methyl]-2-methoxy-N-[[4-(trifluoromethyl)phenyl]methyl]benzamide (KRP-297). The novel crystal of KRP-297 is produced through recrystallization from an alcohol solvent. It is characterized by having diffraction angles (2θ) at at least 9.7°, 15.0°, and 22.5° in X-ray powder diffractometry.

12 Claims, 4 Drawing Sheets

STABLE CRYSTAL OF THIAZOLIDINEDIONE DERIVATIVE AND PROCESS FOR PRODUCING THE SAME

TECHNICAL FIELD

The invention relates to a stable crystal form of 5-[(2,4-dioxothiazolidin-5-yl)methyl]-2-methoxy-N-[[4-(trifluoromethyl)phenyl]methyl]benzamide (KRP-297) represented by a formula (1)

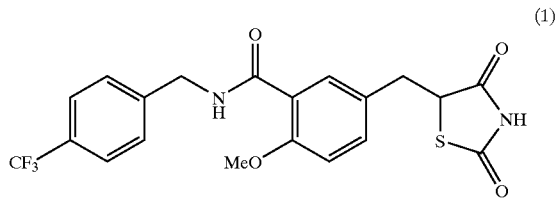

and a process for preparing it.

BACKGROUND TECHNIQUE

KRP-297 has very excellent glucose-lowering activity and is a useful compound as an hypoglycemic agent and an insulin sensitizer (M. Nomura et al, Bioorg. Med. Chem. Lett., 9 (1999) 533–538). At the beginning, it was prepared through a process disclosed in Japanese Kokai Hei 9-48771.

SUBJECT TO BE SOLVED BY THE INVENTION

The objective is to find out crystals homogeneous and excellent in stability and to establish a process for preparing them, in order to prepare KRP-297 on an industrial scale.

DISCLOSURE OF THE INVENTION

With the study and development of the preparative process of KRP-297, the inventors have found that novel crystals different from those having been obtained through conventional process (Japanese Kokai Hei 9-48771) can be obtained, leading to the completion of the invention. Namely, it has been confirmed that, by additionally recrystallization of the crystals (old form crystals) of KRP-297 obtained through conventional processes (for example, Japanese Kokai Hei 9-48771 etc.) from a suitable solvent, they are converted to more homogeneous and more stable novel crystals than conventional ones.

The novel crystals of KRP-297 are characterized by exhibiting the diffraction angles (2θ) at at least 9.7°, 15.0° and 22.5° in the X-ray powder diffraction.

The novel crystals of KRP-297 of the present invention can usually be obtained in good reproducibility by recrystallization of the crude crystals obtained after completion of reaction from a suitable solvent.

As the solvents to be used for recrystallization, lower alcohols such as ethanol, water-containing lower alcohols, common organic solvents, mixed solvents if need be, and the like can be mentioned. Preferable solvent is ethanol or isopropyl alcohol.

The novel crystals of the invention have no hygroscopicity and make it possible to supply stably in terms of preparation, which is very advantageous for the industrial production of KRP-297.

THE BEST MODE FOR WORKING THE INVENTION

EXAMPLE

Figure 1:
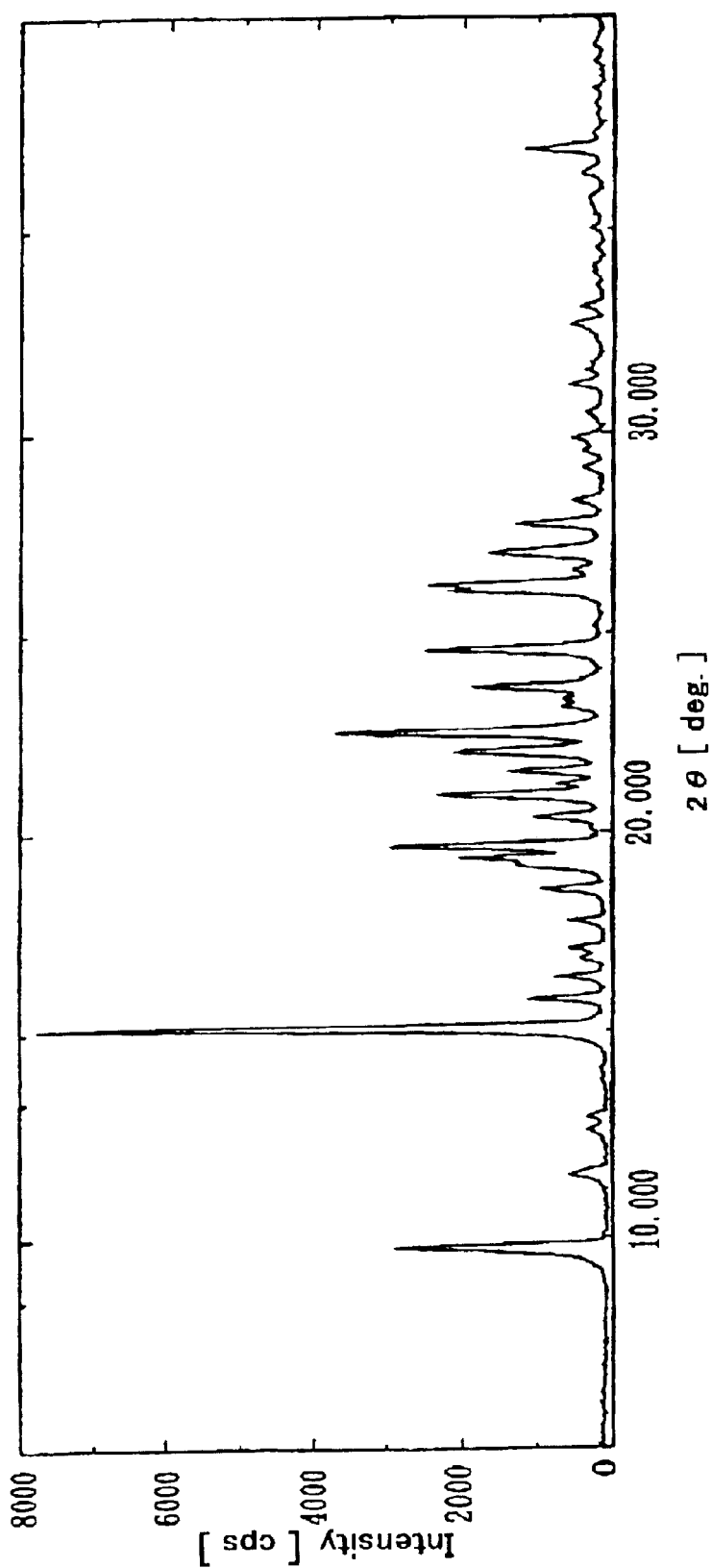
FIG. 1 The X-ray powder diffraction diagram of the inventive novel crystals.

In following, examples will be shown to illustrate the invention in more detail, but the invention does not undergo any restriction by these examples.

Example 1

To 49 mL of dichloromethane were added 6.30 g of triethylamine and 7.00 g of 5-[(2,4-dioxothiazolidin-5-yl) methyl]-2-methoxybenzoic acid. After 2.71 g of ethyl chlorocarbonate were added, the mixture was stirred for 10 minutes. Further, 4.59 g of 4-trifluoromethylbenzylamine were added and the mixture was stirred for 1 hour. After washed the reaction mixture with water, solvent was distilled off and to the residue were added 109 mL of water and 33 mL of ethanol, to which solution 2 mol/L hydrochloric acid was added dropwise to adjust to pH 2.0. The precipitated crystals were collected by filtration and washed with water to obtain 10.25 g of crude crystals. By recrystallizing 10.25 g of crude crystals twice from 90% ethanol, 6.49 g of 5-[(2,4-dioxothiazolidin-5-yl) methyl]-2-methoxy-N-[[4-(trifluoromethyl)phenyl]methyl] benzamide (KRP-297) were obtained (yield 61.3%).

mp. 193–195° C.

Example 2

To 35 mL of isopropyl alcohol dissolving 5.00 g of 5-[(2,4-dioxothiazolidin-5-yl)methyl]-2-methoxybenzoic acid and 4.50 g of triethylamine, 2.12 g of ethyl chlorocarbonate were added dropwise at −5 to 0° C. with stirring. After stirring the mixture for 10 minutes at −5 to 0° C., a solution dissolving 3.27 g of 4-trifluoromethylbenzylamine into 15 mL of isopropyl alcohol was added dropwise to the mixture at −5 to 0° C. After the addition, the mixture was warmed and stirred for 1 hour at 25 to 35° C. Then, the temperature was raised to 60° C. and, after 4.83 mL of 24.5% aqueous solution of sodium hydroxide were added thereto, the mixture was cooled to 3° C. and the precipitated sodium salt was collected by filtration, which was then washed with 15 mL of isopropyl alcohol.

The sodium salt obtained was dissolved into a mixed solution of 78 mL of water and 59 mL of isopropyl alcohol and the solution was adjusted to pH 6.95 with 1 mol/L hydrochloric acid. After cooling it to 6° C., the precipitated crystals were collected by filtration, which were then washed with 23 mL of water. These were dried at 40° C. with blowers to obtain 6.59 g (yield 84.6%) of crude crystals.

These crude crystals were recrystallized from 132 mL of 90% ethanol and then dried at 40° C. under reduced pressure to obtain 6.02 g (yield 77.3%) of KRP-297.

mp. 195–196° C.

Example 3

To 36.3L of isopropyl alcohol dissolving 5.20 kg of 5-[(2,4-dioxothiazolidine-5-yl)methyl]-2-methoxybenzoic acid and 4.68 kg of triethylamine, 2.11 kg of ethyl chlorocarbonate were added dropwise while keeping it at −5 to 0° C., under stirring. After stirring it for 10 minutes at −5 to 0° C., a solution dissolving 3.24 kg of 4-trifluoromethylbenzylamine into 15.6L of isopropyl alcohol was added dropwise thereto while keeping the same temperature. After the completion of dropwise addition, the mixture was warmed and stirred for 1 hour at 25 to 35° C. Then, 20.8L of isopropyl alcohol were added thereto, followed by adding 5.0L of 24.5% aqueous solution of sodium hydroxide. The mixture was cooled to under 10° C., stirred for 1.5 hours, and the precipitated sodium salt was collected by filtration, which was then washed with 15.6L of isopropyl alcohol. From the value of drying loss, 7.78 kg (91.4%) of the sodium salt of KRP-297 were obtained.

The sodium salt obtained was dissolved into a mixed solution of 77.8L of water and 72.9L of isopropyl alcohol, and 1 mol/L hydrochloric acid was added dropwise thereto at 0 to 10° C. to adjust to pH 2.0.

The solution was stirred for 1.5 hours at 0 to 10° C. and the precipitated crystals were collected by filtration, which were then washed with 81.1L of water. From the value of drying loss, 6.12 kg (75.5%) of KRP-297 were obtained. These crude crystals were added to a mixed solution of 28.6L of water and 122L of isopropyl alcohol and heated to over 70° C. to dissolve, which was then filtered while hot and washed with a mixed solution of 2.4L of water and 9.8L of isopropyl alcohol. The mixed solutions were combined, allowed to cool to room temperature, and stirred for 15 hours. The precipitated crystals were washed with 18.4L of isopropyl alcohol, drained, and then dried at 40° C. under reduced pressure to obtain 5.32 kg (yield 65.6%) of KRP-297.

mp. 195–196° C.

Example 4

Into 119L of 90% ethanol were dissolved 5.97 kg of old form KRP-297 crystals (mp. 176.0–177.5° C.) obtained through the conventional process (Example 39 of Japanese Kokai Hei 9-48771) under heat. After filtered while hot, the residue was washed with 12L of 90% ethanol and the filtrates were cooled to room temperature.

The precipitated crystals were collected by filtration and washed with 18L of ethanol. These were dried at 40 to 60° C. to obtain 5.11 kg (85.6%) of novel crystals of KRP-297.

mp. 195° C.

Example 5

Measurement of X-Ray Powder Diffraction

Figure 2:
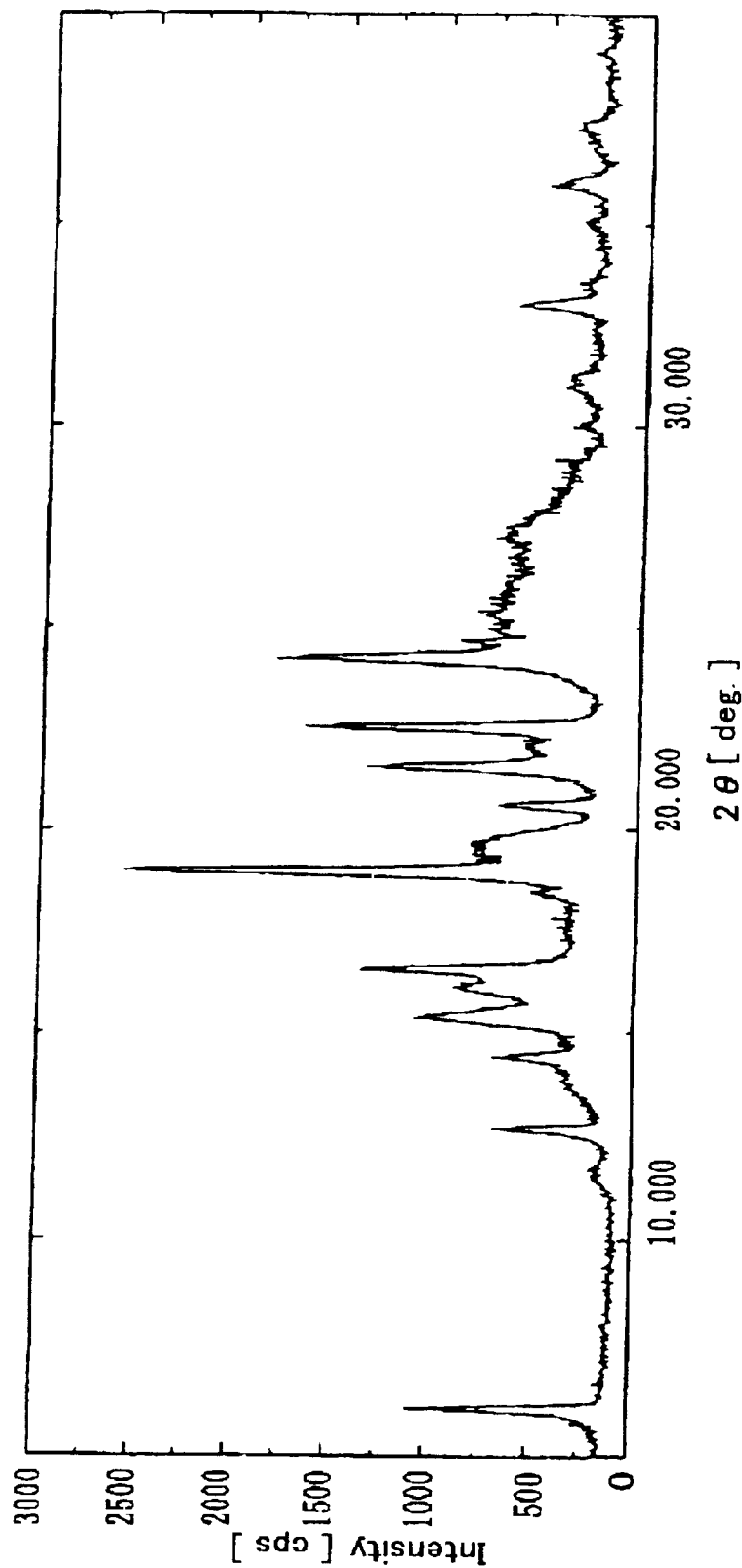
FIG. 2 The X-ray powder diffraction diagram of the crystals through conventional process.

The X-ray powder diffraction was measured by CuKα ray, using a model X-ray diffractometer (Rigaku Co.). The diffraction angle (2θ) and the relative intensity (cps) for the crystals of a compound in example are shown in FIG. 1. The X-ray powder diffraction pattern for the crystals obtained through the conventional process is shown in FIG. 2. As a result, the crystals obtained in example of the invention exhibit a characteristic diffraction pattern at at least 2θ=9.7°, 15.0° and 22.5°, which differs from that of conventional crystals.

Example 6

Thermal Analysis

Using the thermal analysis apparatus (Rigaku Denki; TAS-200), the thermal stability of the crystals were examined.

Figure 3:
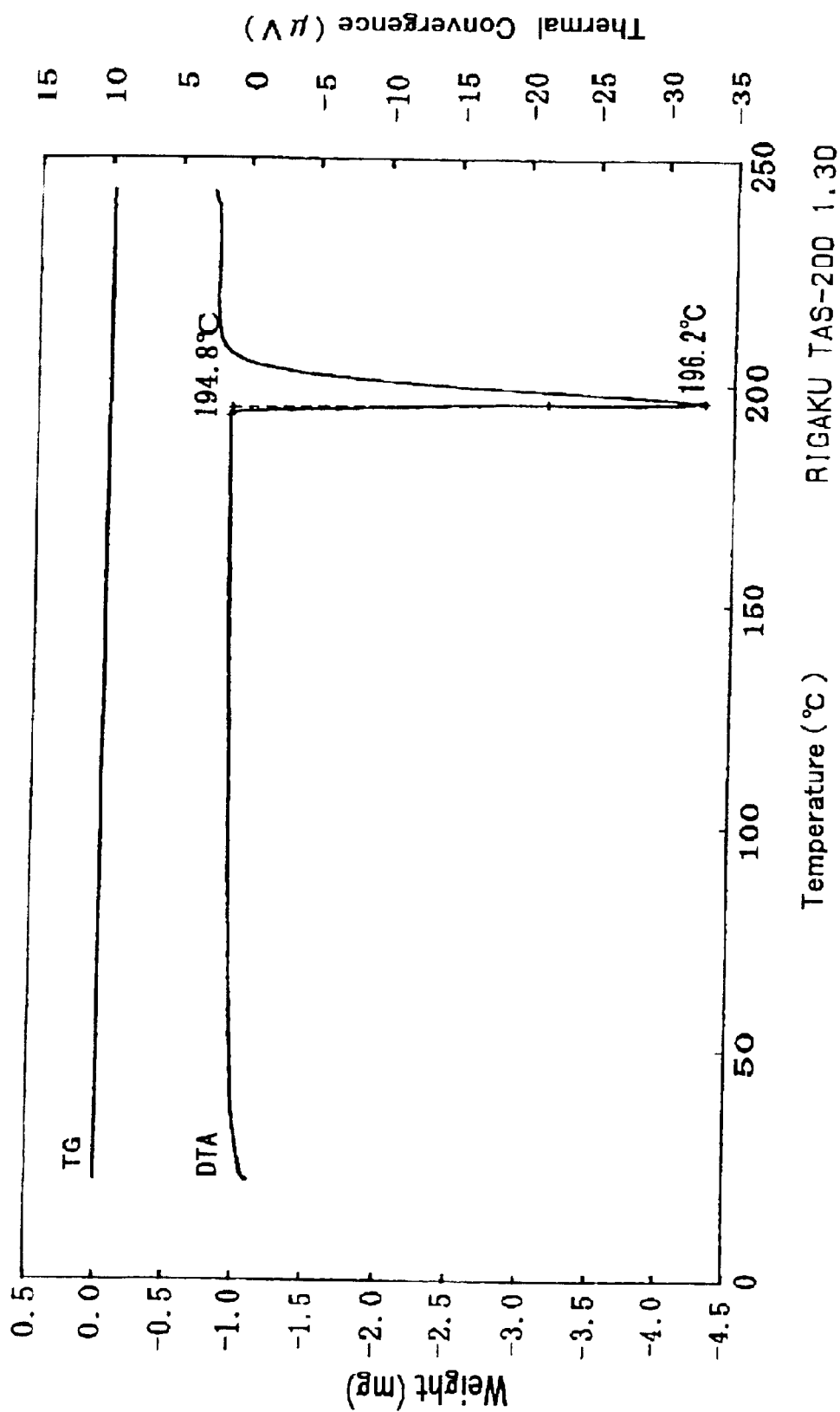
FIG. 3 The thermal analysis diagram of the inventive novel crystals.
Figure 4:
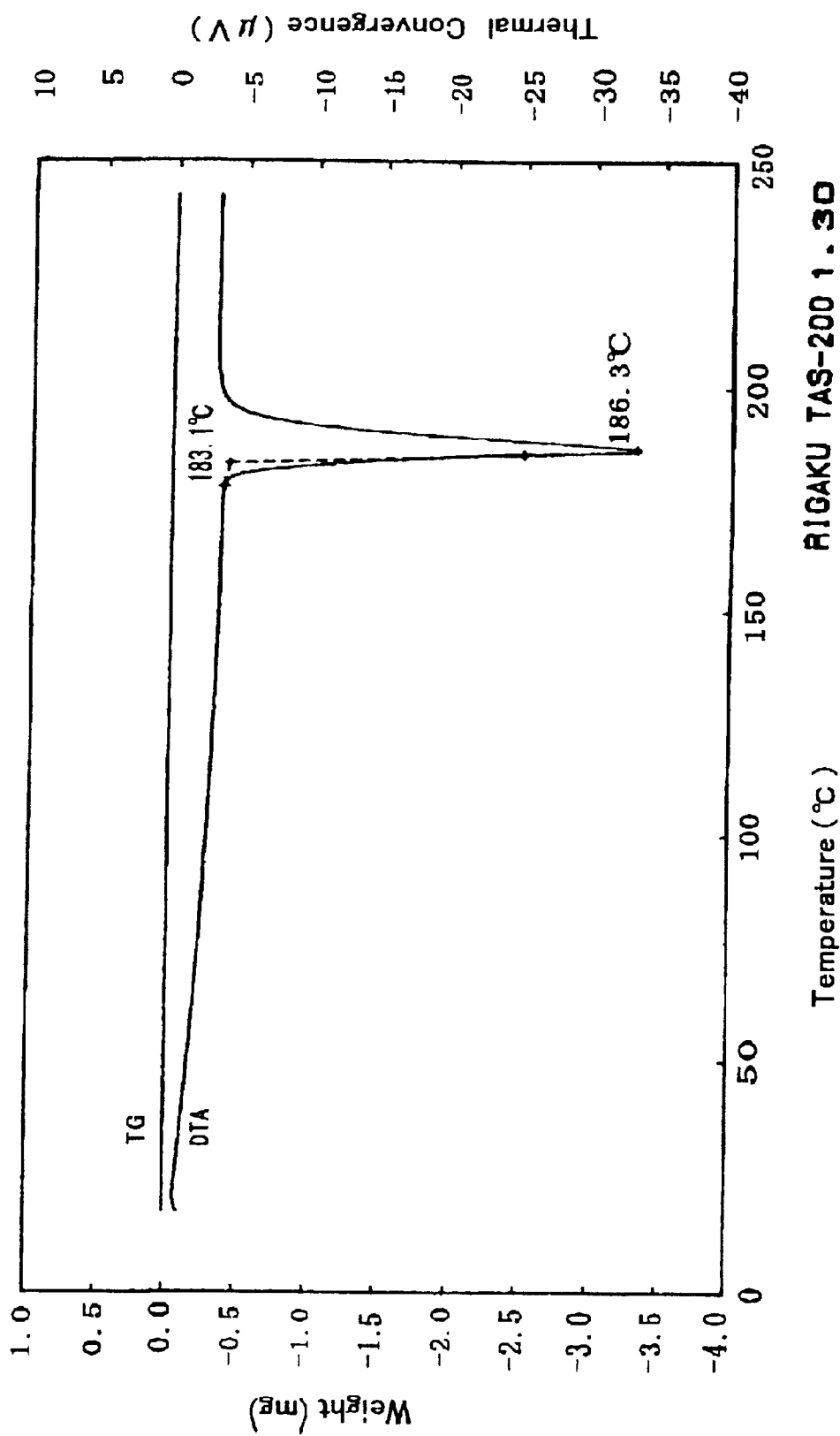
FIG. 4 The thermal analysis diagram of the crystals through conventional process.

The thermal analysis chart for the novel crystal of KPR-297 was shown in FIG. 3, while the thermal analysis chart for the crystal obtained by the conventional method was shown in FIG. 4.

In the novel crystal, endothermic phenomena were observed from 194.8° C. and the endothermic peak was recognized at 196.2° C. On the other hand, the endothermic peak of conventional crystals was 186.3° C.

From this fact, it has become apparent that the novel crystal is one which is more thermally stable, compared with the conventional crystal.

APPLICABILITY ON INDUSTRIES

By additionally recrystallizing the crystals of KRP-297 obtained through conventional process from an alcoholic suitable solvent, homogeneous and more stable novel crystals were obtained. The homogeneous and more stable novel crystals provided according to the invention have no hygroscopicity and make it possible to supply stably in terms of preparation, which is very advantageous in the industrial production of KRP-297.

What is claimed is:

1. A crystal of 5-[(2,4-dioxothiazolidin-5-yl)methyl]-2-methoxy-N-[[4-(trifluoromethyl)phenyl]methyl]benzamide having diffraction angles (2θ) at least at 9.7°, 15.0° and 22.5° in the X-ray powder diffraction.

2. A process for preparing the crystal of claim 1, comprising:

recrystallizing 5-[(2,4-dioxothiazolidin-5-yl)methyl]-2-methoxy-N-[[4-(trifluoromethyl)phenyl]methyl]benzamide from a solvent.

3. The process of claim 2, wherein the solvent is at least one of a lower alcohol or a water-containing lower alcohol.

4. The process as claimed in claim 2, wherein the solvent is ethanol.

5. The process as claimed in claim 2, wherein the solvent is a mixture of ethanol and water.

6. The crystal as claimed in claim 1, having no hygroscopicity.

7. The crystal as claimed in claim 1, having an endothermic peak at 196.2° C.

8. The process as claimed in claim 2, wherein the recrystallizing is carried out twice.

9. The crystal of claim 1, having a melting point of from 193 to 195° C.

10. The process as claimed in claim 2, wherein the solvent is isopropyl alcohol.

11. The process as claimed in claim 2, wherein the solvent is a mixture of isopropyl alcohol and water.

12. The process as claimed in claim 2, wherein recrystallizing includes dissolving crude crystals in the solvent with heating to form a hot solution, filtering the hot solution to form a filtrate, cooling the filtrate to room temperature to precipitate crystals, collecting the precipitated crystals by filtration, and and washing the collected crystals with the solvent.

* * * * *